(12) United States Patent
Bader

(10) Patent No.: US 6,605,463 B1
(45) Date of Patent: Aug. 12, 2003

(54) ROLLING MOUNT FOR A REACTOR

(76) Inventor: Augustinus Bader, Hinter den langen Hofen 16, 31275 Immensen (DE)

( * ) Notice: Subject to any disclaimer, the term of this patent is extended or adjusted under 35 U.S.C. 154(b) by 101 days.

(21) Appl. No.: 09/719,039

(22) PCT Filed: Apr. 7, 2000

(86) PCT No.: PCT/DE00/01062
§ 371 (c)(1),
(2), (4) Date: Jan. 29, 2002

(87) PCT Pub. No.: WO00/61271
PCT Pub. Date: Oct. 19, 2000

(30) Foreign Application Priority Data
Apr. 7, 1999 (DE) .......................................... 199 15 611

(51) Int. Cl.[7] .............................................. C12M 1/10
(52) U.S. Cl. ............................... 435/298.2; 435/303.3; 422/130; 366/214
(58) Field of Search .......................... 435/298.2, 289.1, 435/299.2, 303.3; 366/208, 209, 213, 214, 216, 217, 218, 233; 472/130

(56) References Cited

U.S. PATENT DOCUMENTS

| | | |
|---|---|---|
| 1,002,347 A | 9/1911 | Wemer |
| 3,090,604 A | 5/1963 | Wheeler |
| 3,439,901 A * | 4/1969 | McCulloch .................. 366/233 |
| 4,237,733 A | 12/1980 | Kolb et al. |
| 4,461,578 A | 7/1984 | Tiebout |
| 4,479,720 A | 10/1984 | Mochida et al. |
| 5,266,273 A | 11/1993 | Coombs |
| 5,322,358 A * | 6/1994 | Coho et al. .................. 366/214 |
| 5,380,662 A | 1/1995 | Robbins et al. |
| 5,426,037 A | 6/1995 | Pannell et al. |
| 6,066,497 A * | 5/2000 | Powell ..................... 435/286.5 |

FOREIGN PATENT DOCUMENTS

| | | |
|---|---|---|
| DE | OS 2 202 057 | 8/1972 |
| DE | 98 028 | 6/1973 |
| DE | GM 77 19 795 | 12/1977 |
| DE | 28 31 085 | 3/1979 |
| DE | 911 27 38 U | 10/1991 |
| DE | 692 18 506 T2 | 10/1997 |
| EP | 0 540 905 A1 | 5/1993 |
| FR | 963 775 A | 1/1950 |
| FR | 963 775 | 1/1950 |
| GB | 2 002 814 | 2/1979 |
| WO | WO 92/22634 | 12/1992 |
| WO | WO 99/04270 | 1/1999 |

* cited by examiner

Primary Examiner—William H. Beisner
(74) Attorney, Agent, or Firm—Whitham, Curtis & Christofferson, PC

(57) ABSTRACT

The invention relates to a mount for a container, e.g., a cell culture flask or a reactor with supply connections, for instance a bioreactor, that is chiefly designed for treatment in a rolling cabinet or in a chamber having rolling devices. The device has one or several locating elements for containers or reactors and an outlet form capable of rolling. This makes it possible to treat a container or reactors not capable of rolling in the rolling cabinet. An appropriate form of the mount makes it possible to rotate the mount in additional spatial directions during treatment in the rolling cabinet. The reactor can be supplied with liquid media and the temperature can be adjusted inside the mount.

11 Claims, 6 Drawing Sheets

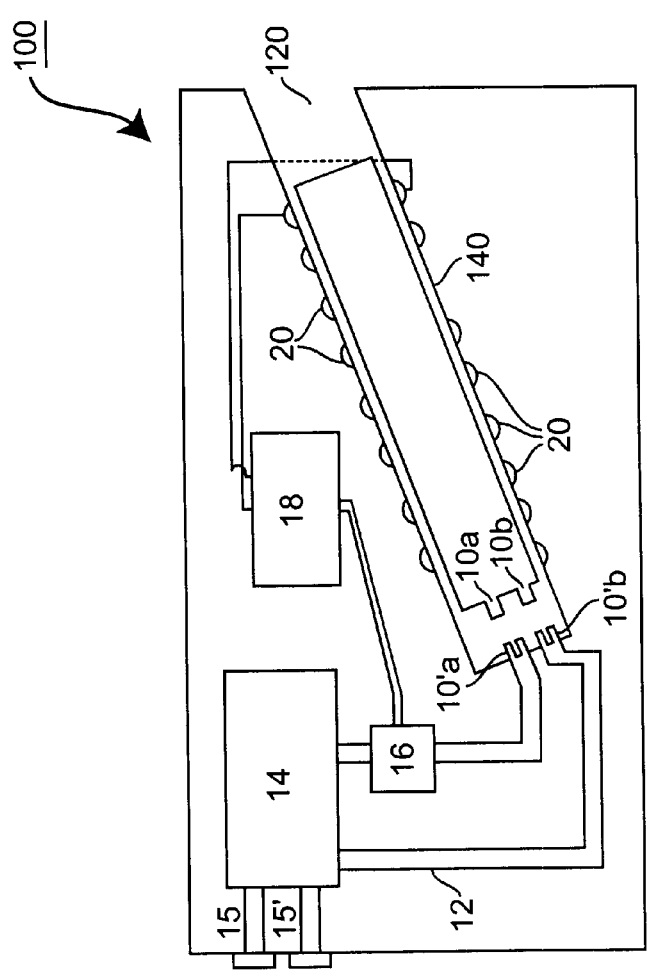
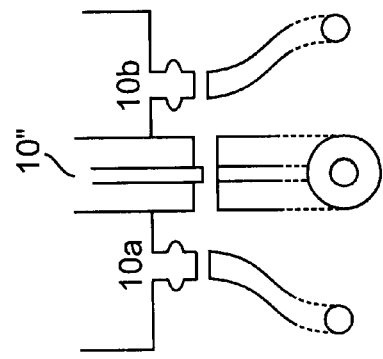
Figure 4
Figure 4A

ROLLING MOUNT FOR A REACTOR

BACKGROUND OF THE INVENTION

1. Field of the Invention

The present invention generally relates to a mount for container, that is chiefly designed for treatment in a rolling cabinet or in a chamber having rolling devices.

2. Background Description

The invention relates to a mount for at least one container used in implementation of a treatment during which the container is turned or rolled. The container in question can be any vessel, e.g., a flask, a rolling flask, a sealed reagent tube, or the like.

The invention particularly relates to a mount for the treatment of rolling flasks, cell cultures, or reaction vessels, but also of bioreactors, in a rolling cabinet or a space with rolling devices.

Known to the prior art are rolling flasks that are specially provided for insertion into so-called rolling cabinets, in which the rolling flasks are continuously kept in motion by being rolled, while certain external conditions are maintained. In this way, the contents of the rolling flask are kept in continuous rolling motion. In general, the rolling cabinet can be adjusted for temperature, so that the container interior being treated can be kept at a constant temperature, e.g., a physiological temperature.

In a rolling cabinet the inserted flask is rotated around its longitudinal axis. With this kind of rolling motion, therefore, it is not possible to distribute or mix the contents of the flask or container in a truly uniform manner. This applies particularly to reactors such as bioreactors, since here the mixing can be rendered additionally difficult by installed components.

The invention is therefore based on the problem of providing a device with the aid of which containers, flasks, reactors, and the like that are to be treated in a rolling cabinet can be rotated in more than one spatial direction, while making it possible for reactors with supply connections to be simultaneously supplied by these connections.

SUMMARY OF THE INVENTION

To solve this problem the invention provides for a mount for at least one container used to implement a treatment in which the container is turned or rolled, which mount has at least one seat for the container, and whose external shape is either cylindrical, with the primary longitudinal axis of the seat(s) resting at an angle to the axis of the cylinder, or is ball-shaped or spherical.

This mount for the seat and mounting of at least one reactor, particularly a bioreactor, that exhibits power connections will ideally include a reservoir and a line system for supplying the one or more reactors with at least one liquid or gaseous medium, while the line system will open into couplings that are adapted to the supply connections of the reactor and are positioned at the corresponding seat. Also possible are a plurality of reservoirs and line systems that are separately assigned to the individual reactors.

As an alternative, the problem is solved with a mount for at least one reactor exhibiting power supplies, in implementation of a treatment involving rotating or rolling the reactor, which mount has at least one seat for at least one reactor and includes a reservoir and a line system for supplying the one or more reactors with at least one liquid or gaseous medium, while the line system opens into couplings that are adapted to the supply connections of the reactor and are positioned on the corresponding seat, and which mount either has an external shape that permits rolling or is suspended in turning fashion in a frame and is provided with, or are attached to, a rotating drive.

The container or reactor can be secured inside the seat(s) with suitable means for attachment, or can be merely inserted or plugged in, in which case the frictional force will provide a secure mount.

In an alternative design of the mount, the external shape that permits rolling will preferably be cylindrical, spherical, or ball-like. If the outer shape of the mount is cylindrical, it is particularly advantageous if the primary longitudinal axis of the seat lies at an angle to the rotating axis of the rolling mount. The seat is then advantageously positioned in such a way that the inserted container rests at a diagonal to the longitudinal axis of the cylinder around which the rotating cabinet turns. In this way the rotating motion exercised on the container will be reinforced with a swinging motion from one end of the inserted container to other as soon as the container in the mount is rolled in a rolling cabinet.

Different angles between 0 and 90° can be used between the seat, and thus the inserted container, and the (primary) rolling axis of the rolling mount.

The mount can also be non-uniform in design, as long as it is capable of rolling. If the mount is spherical or ball-shaped, a random motion between various spatial axes will arise in the rolling cabinet. The random motion can be further supported by projecting knobs applied on the outside on the ball-shaped mount. In place of guide nubs, other kinds of contouring can be used, regardless of the shape of the mount. In the case of a cylindrical mount, eccentric rings 122, for example, can be applied around the cylinder jacket, as shown in FIG. 6.

For the seat of a flask, e.g., a conventional rolling flask, the seat of the mount will ideally be tube-shaped. The seat can also have any other shape, which will then ideally be adjusted to the external shape of the container or reactor being received.

In one and the same mount, a plurality of seats can be provided for the insertion of a number of containers or reactors.

The mount is used to rotate a rolling container, such as a rolling flask, with a greater degree of freedom than that provided by rotation around its longitudinal axis, or in order to permit a container that is not a rolling one, e.g., a box-shaped container, to be treated in a rolling cabinet. The mount is also used to allow a reactor provided with supply connections to be supplied without difficulty within a rolling cabinet or a rotating apparatus.

In a particular elaboration of the invention, the mount is provided with a device for heating or cooling the containers or reactors, or for controlling their temperature with a thermostat. The specialist can design these heating devices in a known manner. For example, heating wires or cooling coils can be positioned inside the mount, particularly around the seats for the container or the reactors, in order to heat or cool the seats, or to control their temperature with a thermostat. For thermostat control, at least one temperature sensor is also necessary; it can also be housed, along with the corresponding energy supply, inside the mount.

If the mount is equipped with a reservoir and a line system for supplying a reactor via coupling connections, a preferred embodiment provides a pump for circulating the fluid medium inside the line system. If a plurality of reactors are housed in a mount, a number of reservoirs and line systems, including pumps, can also be provided.

In a further elaboration of the invention, at least one energy supply component—e.g., in the form of a battery—can be included per mount for any heating, pumping, or rotating operations performed inside the mount.

The mount can consists of any suitable material, e.g., glass, plastic, metal, or a combination thereof

BRIEF DESCRIPTION OF THE DRAWINGS

The foregoing and other objects, aspects and advantages will be better understood from the following detailed description of a preferred embodiment of the invention with reference to the drawings, in which:

FIG. 1 shows a mount for a cylindrical container, e.g., a culture flask, a reagent tube, or the like;

FIGS. 4 and 4A gives a schematic view of a mount with a seat for a reactor, in longitudinal section;

DETAILED DESCRIPTION OF A PREFERRED EMBODIMENT OF THE INVENTION

Figure 1:
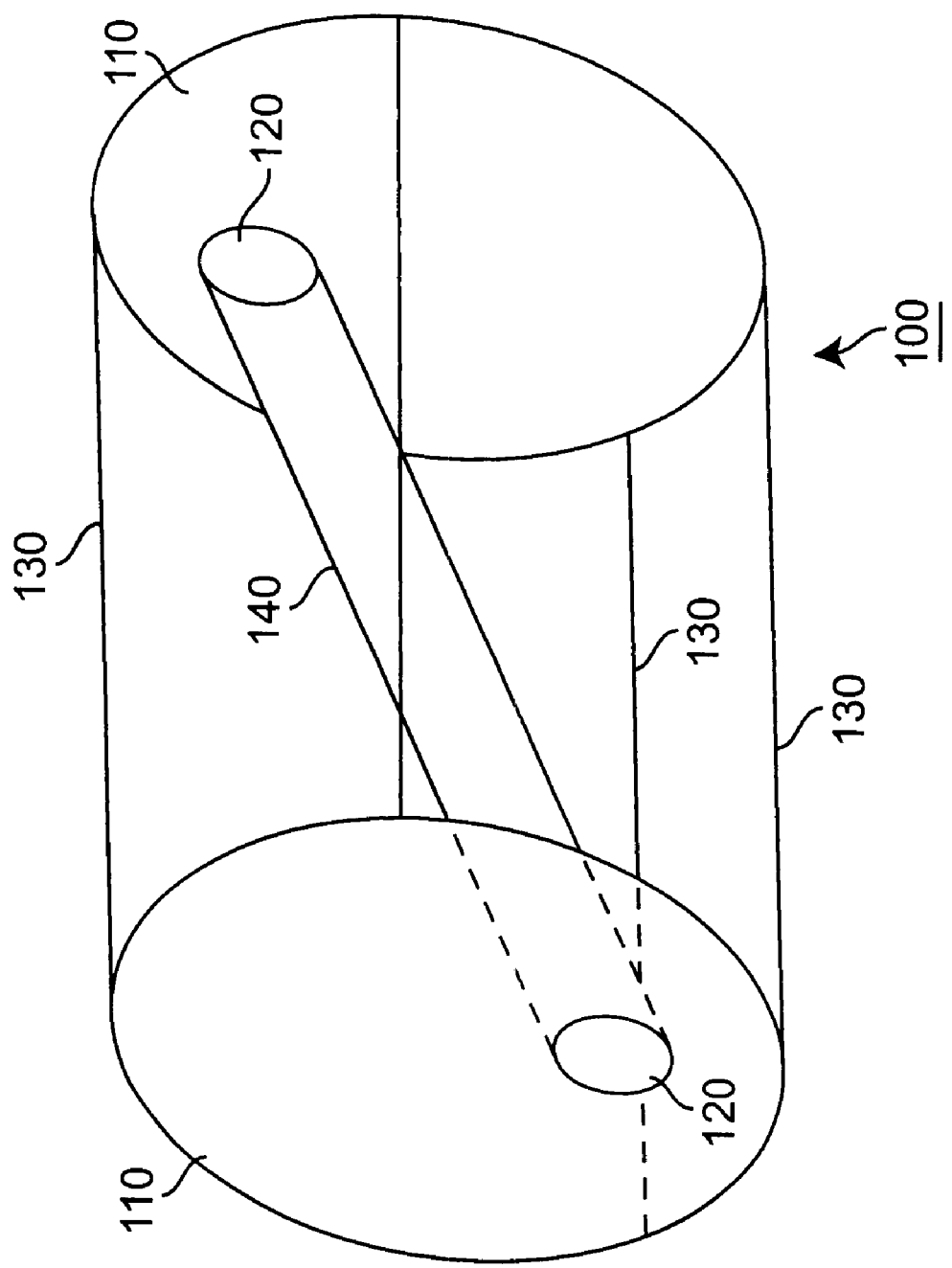

FIG. 1 shows a cylindrical rolling mount 100, in which a culture flask or the like can be inserted during treatment in a rolling cabinet. Because of the mount, the inserted container is subjected to a swinging motion at a diagonal to its longitudinal axis, in addition to the rolling motion. In this embodiment, the mount 100 consists of two disks 110 of glass or plexiglass, which are eccentrically provided with two oval (cylindrical) openings 120. The openings 120 will ideally be oval if a cylindrical container is used; in this example, the disks 110 are circular, but could also have a different shape, e.g., an elliptical one. In the present example, the disks 110 are connected by means of a plurality of rods 130, though they could be connected by means of a closed cylinder casing. The disks 110 are connected in such a way that in projection the openings 120 lie opposite each other in offset fashion. Running between the openings 120 is a tubular hole 140, into which the given container can be inserted. Together, the openings 120 and the tube 140 form the recess into which the container is inserted. The longitudinal axis of the container, which is not depicted in the drawing, then runs at an angle to the longitudinal axis of the mount 100, whose overall shape is cylindrical. The mount 100, together with the container, forms a configuration that can be placed in a rolling cabinet. In the case of treatment in the rolling cabinet, the container is subjected to a rolling motion around its longitudinal axis and, at the same time, to a swinging motion at an angle to its longitudinal axis. As a result, the container contents, e.g., a culture medium, with the cells contained therein, can be intensively and uniformly distributed and, e.g., brought into contact with a substrate also found in the container.

Figure 2:
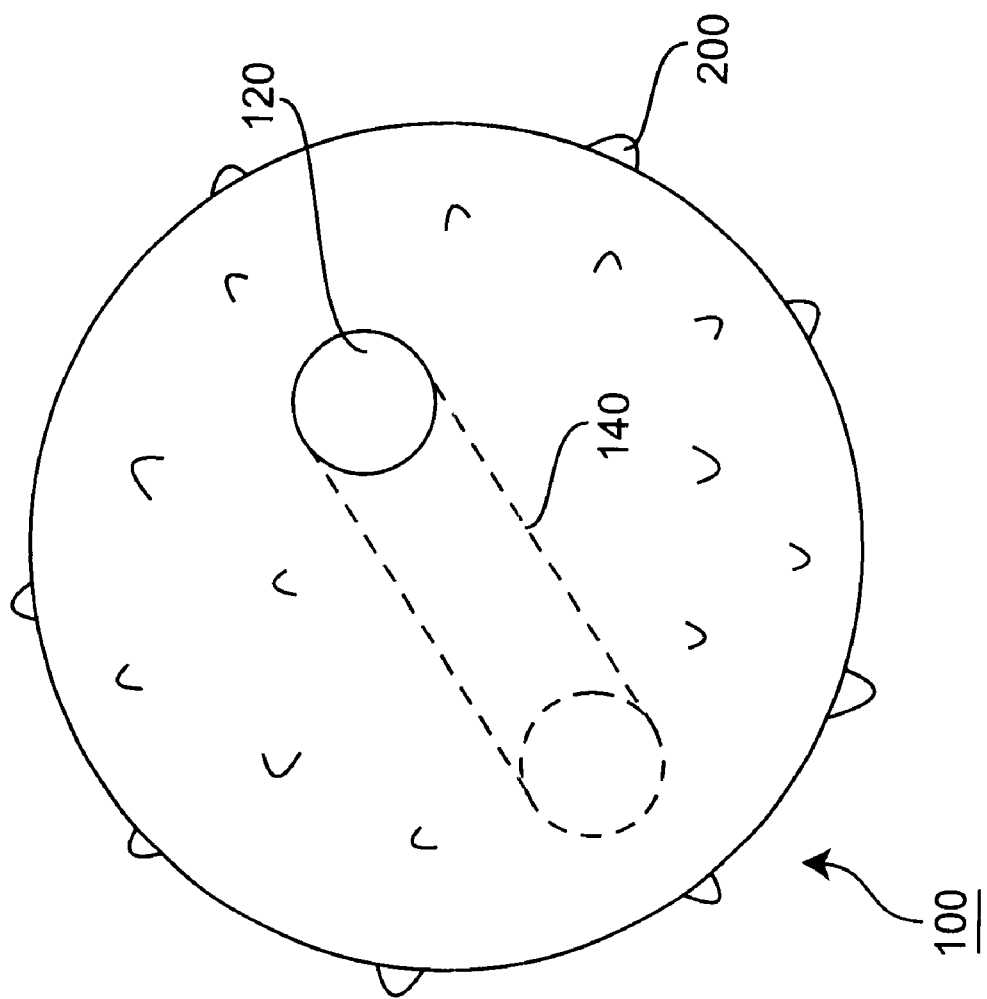
FIG. 2 shows a spherical mount with projecting knobs and a tube-shaped recess.

FIG. 2 shows a spherical mount 100 with two circular openings 120 and a tubular opening 140 that runs through the center of the sphere. The tube 140, together with the openings 120, jointly forms a recess for insertion of a container, which is to be treated in a rolling cabinet held in this mount. In order to constantly and randomly change the sphere's direction of motion within the rolling cabinet, projecting knobs 200 are applied to the outer wall of the spherical mount 100. This prevents any preferred direction from establishing itself during rolling. The sphere could also consist of, e.g., a wire grating.

Figure 3:
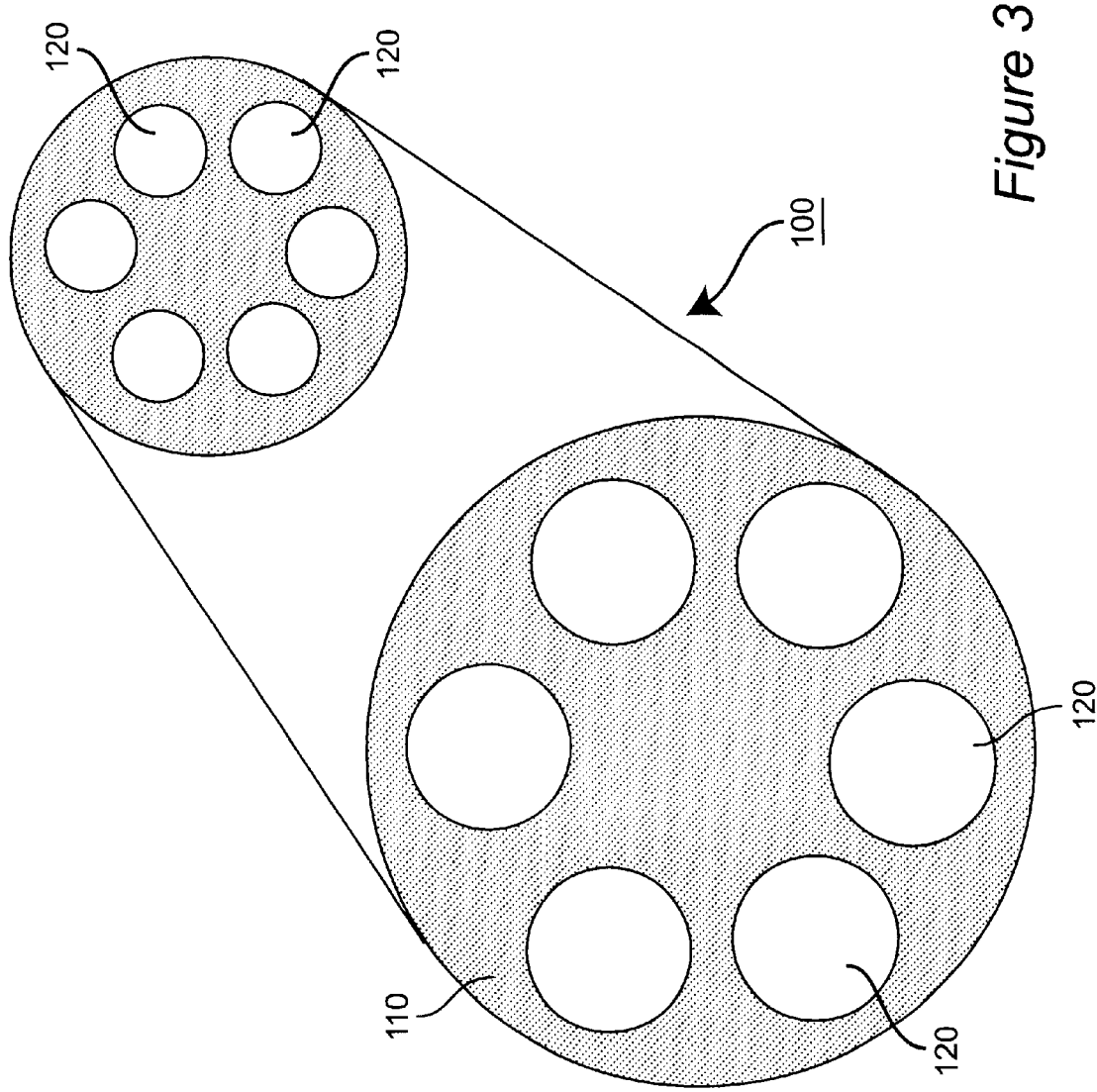
FIG. 3 shows a barrel-shaped mount for a number of cylindrical containers/flasks.

FIG. 3 shows a barrel-shaped mount 100 for several cylindrical containers, e.g., rolling flasks, reaction vessels, or the like. In principle, this mount 100 corresponds to the cylindrical mount from FIG. 1, with the difference that a number of openings have been furnished in the two lateral disks 110, so that a plurality of elongated cylindrical containers—in this embodiment, a maximum of 6 pieces—can be inserted into the cylinder. Here the containers should be inserted into the cylinder in such a way that their axes run aslant the rolling axis if the additional swinging motion diagonal to the longitudinal axis is desired, i.e., the two ends of a cylindrical container will be inserted into facing, but offset openings 120; if this is not the case, the containers can lie parallel to the rolling axis.

FIG. 4 gives a schematic view, in longitudinal section, of a mount designated 100 in its entirety. This drawing depicts only a seat for a container or reactor, specifically a tube 140, which can be loaded from an opening 120. The mount 100 consists of a cylinder that is externally sealed in order to protect the components (which are described below in greater detail) contained therein. Shown inside the tube-shaped seat 140 is an inserted reactor A, which has supply connections 10a, 10b, e.g., sterile couplings for a culture medium (culture medium port). The supply connections 10a, 10b lie opposite fitted coupling connections 10'a, 10'b, which are connected to the line system 12 by means of which the reactor A is supplied when the supply connections 10a, 10b and the corresponding coupling connections 10'a, 10'b are connected, e.g., by means of a plug connection. The line system 12 is connected to a reservoir 14 to supply the liquid or gaseous medium with which the reactor A is fed. The reservoir 14 can be filled or emptied through the connections 15, 15'. It can be composed of two separate containers for fresh medium and for waste. In the present exemplary embodiment, a pump 16 is positioned in the line system 12—e.g., a hose pump—which is connected to a battery or accumulator 18 to supply power. The battery 18 simultaneously provides current for the heating wires 20, which surround the tube 140 in spiral fashion. The seat that houses the reactor A can be heated in this manner.

In the example shown in FIG. 4 the reactor A has two connections 10a and 10b, i.e., an inlet and outlet for a liquid supply medium. More connections can be present, however, for example, for N2/O2/CO2 supplies. Other elements than those shown in FIG. 4 can be integrated into the mount, for example, devices for cryoprotection, a thawing system, or one or several chips for monitoring and control of the individual functions.

The detail shown in FIG. 4a schematically depicts the lower section of a reactor with three connections and a primary coupling capability, where connections 10a and 10b are simple inlets and outlets, while the supply connection 10" is a coaxial connection. The inlet and outlet relationships are shown beneath the connections.

FIG. 5 shows in 5a a configuration for rolling any desired mount, and in 5b a configuration for rotating a mount within a frame.

Figure 5B:
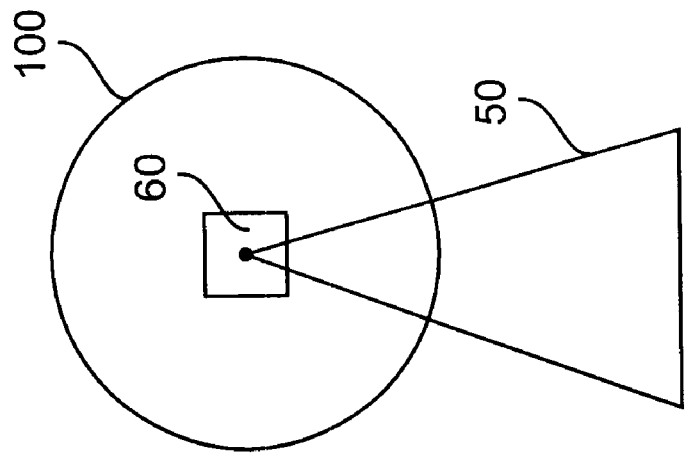
FIG. 5B shows a design for rotating a mount in a frame.
Figure 5A:
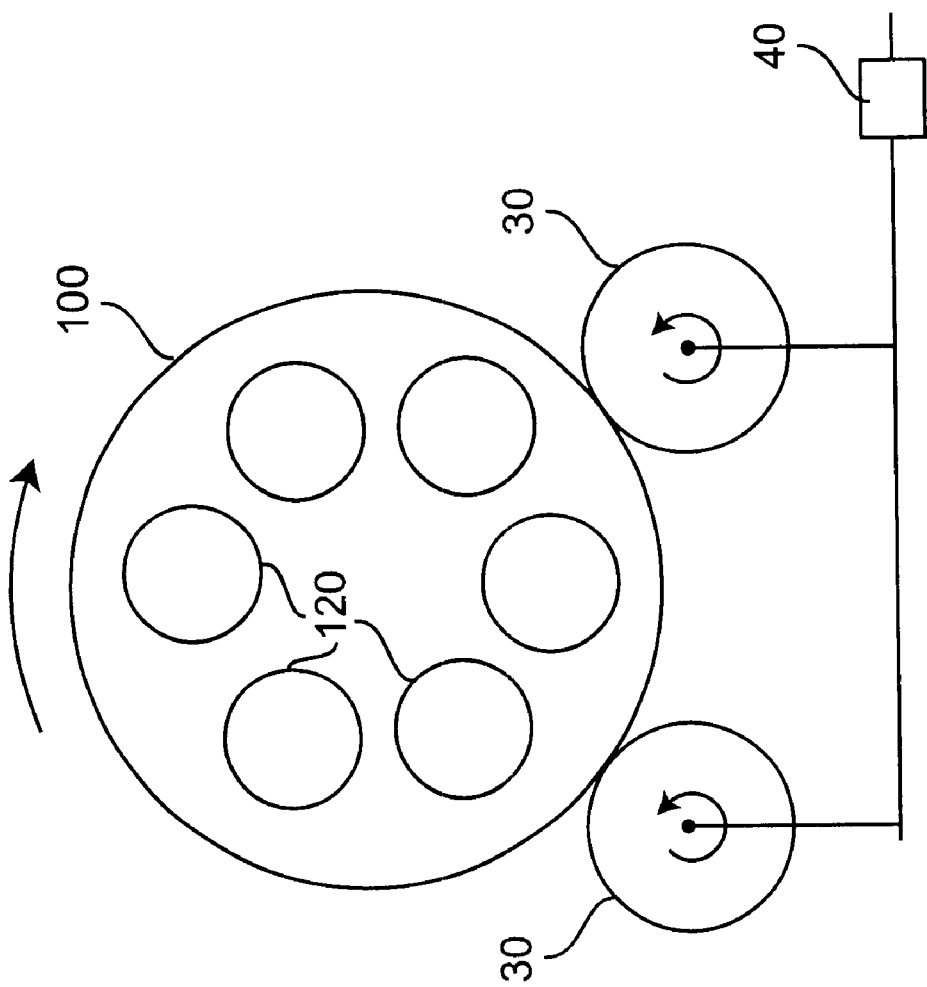
FIG. 5A shows a design for rolling a mount.
Figure 6:
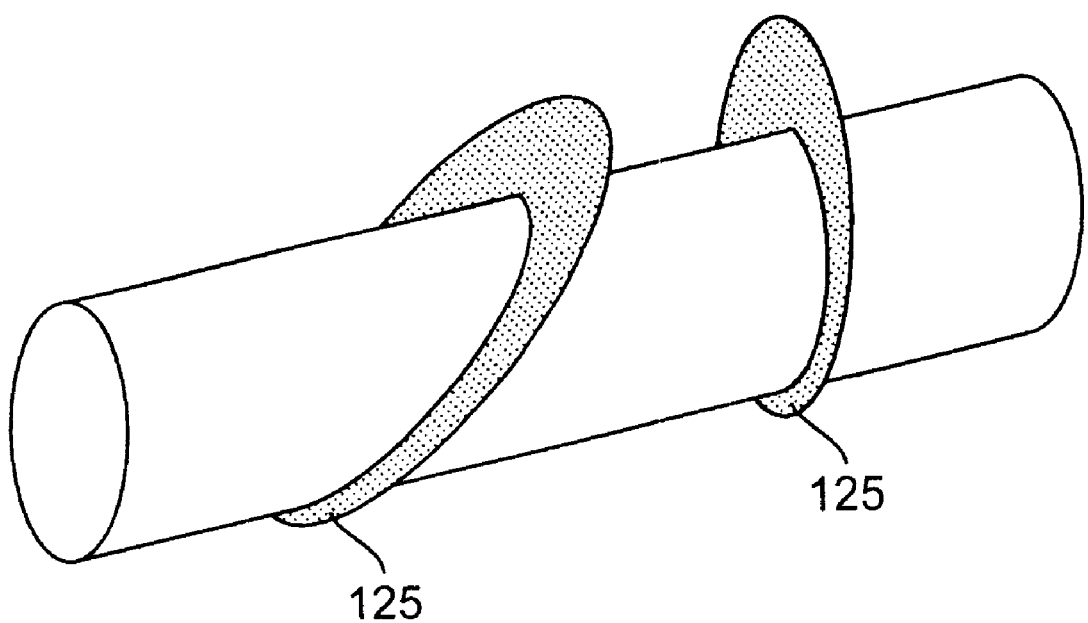
FIG. 6 shows eccentric rings 125 on a case of a cylindrical mount.

FIG. 5a depicts a cylindrical mount 100, here with six recessed openings 120, in front view. The cylinder-shaped mount 100 rests on rollers 30 that are driven and rotated by a drive 40 using any desired transmission.

FIG. 5*b* shows another cylinder-shaped mount 100, whose cylindrical axis is supported by a frame in such a matter as to permit rotation. Positioned on the rotating axis is a schematically depicted rotating drive 60, whose other connections are not shown in the drawing. The mount 100 otherwise resembles that shown in FIG. 4.

I claim:

1. A mount (100) for at least one reactor for implementing a treatment in which the reactor is rotated or rolled, wherein said mount either has an external shape that permits it to roll or is suspended in a frame and is provided with, or connected to a rotating drive, wherein the mount (100) comprises:
at least one seat (140) for at least one reactor,
a reservoir (14) to supply the liquid or gaseous medium, and
a line system (12) for supplying the one or more reactors with at least a liquid or gaseous medium, while the line system (12) opens into couplings (10*a*, 10*b*) that are adapted to the supply connections (10*a*, 10*b*) of the reactor and are positioned at the corresponding seat.

2. A mount according to claim 1, wherein said reactor is a bio-reactor.

3. A mount according to claim 2, wherein said mount includes a pump for pumping at least one liquid or gaseous medium within the reactor supply lines.

4. A mount according to claim 1, wherein the seat or seats are tube-shaped.

5. A mount according to claim 1, wherein projecting knobs are positioned on a rolling surface or rim of the mount.

6. A mount according to claim 1, wherein eccentric rings are positioned on a rolling outer jacket of the mount.

7. A mount according to claim 1, wherein said mount includes a device for heating or cooling the reactor(s) or for controlling their temperature with a thermostat.

8. A mount according to claim 1, wherein said mount includes an power supply for any heating, pumping, or rotating operations that must be performed.

9. A mount (100) for at least one reactor exhibiting supply connections for implementing a treatment during which the reactor is rotated or rolled, wherein said mount has at least one seat for the one or more reactors,
and has a reservoir and a line system for supplying the one or more reactors with at least a liquid or gaseous medium, while the line system opens into couplings that are adapted to the supply connections of the reactor and are positioned at the corresponding seat, and
the mount either
has a external shape that permits it to roll, or
is suspended in a frame and is provided with, or connected to, a rotating drive.

10. A mount according to claim 9, wherein the external shape that permits rolling is a sphere or a ball or a cylinder.

11. A mount according to claim 10, wherein the primary longitudinal axis of the seat lies at an angle to the rotating axis of the rolling mount.

* * * * *